United States Patent [19]

Schmidt et al.

[11] Patent Number: 4,684,227
[45] Date of Patent: Aug. 4, 1987

[54] BINOCULAR INDIRECT OPHTHALMOSCOPE

[75] Inventors: Otto H. Schmidt; Helmut A. Heine, both of Herrsching; Helmut Rosenbusch, Weilheim, all of Fed. Rep. of Germany

[73] Assignees: Propper Manufacturing Co., Inc., Long Island City, N.Y.; Heine Optotecnik GmbH & Co. KG, Herrsching, Fed. Rep. of Germany

[21] Appl. No.: 695,183

[22] Filed: Jan. 28, 1985

[51] Int. Cl.$^4$ .......................... A61B 3/10; G02B 7/02; G02B 21/06

[52] U.S. Cl. .................................. 351/205; 351/221; 350/518; 350/523

[58] Field of Search ............... 351/205, 214, 211, 221, 351/206; 350/518, 523

[56] References Cited

U.S. PATENT DOCUMENTS 3,963,329 6/1976 Stumpf et al. .
4,196,966 4/1980 Malis .
4,449,797 5/1984 Kocher et al. .
4,568,158 2/1986 Blaha et al. .......................... 351/205

OTHER PUBLICATIONS

Clinical Evaluation of the Small-Pupil Binocular Indirect Ophthalmoscope, Kenneth R. Hovland, M.D., et al, reprinted from the Archives of Ophthalmology, Oct. 1969, vol. 82 copyright 1969, American Medical Association.

Primary Examiner—Rodney B. Bovernick
Assistant Examiner—P. M. Dzierzynski
Attorney, Agent, or Firm—Amster, Rothstein & Ebenstein

[57] ABSTRACT

A binocular indirect ophthalmoscope is disclosed in which the optical observation axes from the examiner's pupils to the patient's pupil and the optical illumination axis from an illumination source to the patient's pupil are varied simultaneously by a single conveniently located lever. Mirrors reflecting the observation axes and the illumination axis are mounted on a common movable holder in fixed relationship to each other. The lever is coupled to the holder to move the holder in the observation plane upon actuation of the lever and thereby adjust both the observation axes and the illumination axis at the same time.

12 Claims, 5 Drawing Figures

BINOCULAR INDIRECT OPHTHALMOSCOPE

BACKGROUND OF THE INVENTION

The present invention relates generally to a binocular stereoscopic viewing device and in particular to a binocular indirect ophthalmoscope for stereoscopic observation of the fundus of the eye.

In binocular ophthalmoscopic examinations, the examiner's pupils and an observation light source must be reflected to the pupil of the eye to be examined. For good stereoscopic vision, images of the examiner's pupils must be separated from each other as far as possible. In order to receive as few interfering reflexes as possible from the cornea of the patient's eye, the image of the light source should be separated as far as possible from the images of the examiner's pupils. These conditions can be met satisfactorily if the pupil of the patient is dilated by the application of a drug. There are, however, cases in which a dilation of the pupil is impossible or impractical, and to stereoscopically view a patient's pupil in such cases, binocular indirect ophthalmoscopes were developed in which relative separation of the images of the examiner's pupils and of the light source can be adjusted to the size of the patient's pupil.

U.S. Pat. No. 4,449,797 (Kocher et al.) discloses a binocular indirect ophthalmoscope comprising an observation unit and an illumination unit connected thereto. The observation unit contains two mirrors arranged in a wedge for reflecting images of the examiner's pupils to the patient's pupil along optical observation axes forming an observation plane extending from the observation unit toward a patient. The two mirrors are displaceable in the observation plane making it possible to alter the angle of convergence of the optical observation axes between the mirrors and the patient's pupil, and hence, the position of the images of the examiner's pupils relative to the patient's pupil. The illumination unit contains another mirror which can be raised, lowered or tilted, to change the optical axis of light projected from the light source and thus the position of the light source relative to the patient's pupil.

A similar ophthalmoscope is described in the article by K.R. Hovland et al. titled "Clinical Evaluation of the Small-Pupil Binocular Indirect Ophthalmoscope", published in "Archives of Ophthalmology", October 1969, Volume 82, pages 466–474. In the ophthalmoscope described in this article, the two observation mirrors are also arranged in a wedge displaceable in the observation plane, and the third mirror for reflecting illumination from the light source is independently displaceable parallel to the observation plane, making it possible to independently adjust the angle of convergence of the images of the examiner's pupils and the position of the image of the light source relative to the patient's pupil.

In both of the above-described ophalmoscopes, the examiner has to actuate two operating controls in order to adjust the optical axes of observation and the optical axis of illumination and position images of the examiner's pupils and the light source within the respective size of the patients's pupil. It is particularly difficult for a less skilled examiner to coordinate the separate operating controls for moving the observation mirrors and the illumination mirror by alternating actuation of the controls in such a way to optimize stereoscopic viewing of the fundus of the patient's eye without interference from disturbing reflections. Adjusting such ophthalmoscopes for narrow pupils of patients is difficult even for an experienced examiner, so that an exact adjustment is frequently dispensed with for reasons of time, and the examiner is satisfied with monocular observation of the fundus of the eye.

U.S. Pat. No. 3,963,329 (Stumph et al.) discloses a binocular indirect ophthalmoscope also of the type having two observation mirrors arranged in a wedge for reflecting the examiner's pupils from respective eyepieces, and an illumination mirror for reflecting light. The illumination axis is adjusted by moving the illumination mirror with one control, and the observation axes are adjusted by moving the eyepieces. Thus, two separate adjustments have to be made to adjust the observation axes and the illumination axis.

U.S. Pat. No. 4,196,966 (Malis) discloses a binocular magnification unit which includes a pyramid-shaped reflector having three reflective surfaces.

OBJECT AND SUMMARY OF THE INVENTION

It is an object of the present invention to provide a binocular stereoscopic viewing device, particularly an indirect ophthalmoscope, in which adjustment of the optical observation and illumination axes can be performed quickly and simply, for stereoscopically viewing and illuminating an object, particularly a pupil of almost any diameter.

The present invention achieves the above and other objects, and comprises, briefly, an arrangement of optical elements along the optical axes both from the user's eyes and from an illumination means on a commonly movable support displaceable along an optical axis extending between the user's eyes and the object to be observed. The support can be displaced by means of a single manually-operated control.

A stereoscopic viewing device according to an embodiment of the invention comprises an observation unit, means for projecting light into the observation unit, spaced eyepieces secured to the observation unit through which a user views an object to be observed, an optical aperture into the observation unit through which light passes between the object to be observed and the interior of the observation unit and optical means disposed in the observation unit for optically coupling the eyepiece and the light-projecting means with the aperature, the optical means including a first optical element optically coupling one eyepiece and the aperature, a second optical element optically coupling a second eyepiece and the aperture, and a third optical element optically coupling the light projecting means and the aperture, means or support structure supporting the first, second and third optical elements for movement together within the observation unit and means for moving the supporting means.

The first, second and third optical elements can comprise first, second and third reflective surfaces, respectively, the supporting means can comprise a holder to which the reflective surfaces are secured in a predetermined, fixed relationship to each other, and the moving means can comprise an operating control and means for securing the holder in the observation unit for displacement relative to the aperture in response to actuation of the operating control. The first and second reflective surfaces can be arranged in a wedge so that the observation axes extend in an observation plane defined by the optical observation axes from the first and second reflective surfaces, the unit being displaceable in the observation plane.

According to one embodiment, the moving means comprises a guideway and a mating guide slidably disposed with respect to each other, one of which is secured to the holder and the other of which is secured to the observation unit, and an operating control coupled to the holder and accessible exteriorly of the observation unit such that actuation of the operating control displaces the holder together with the three optical elements.

The operating control can be a lever pivotally coupled to the observation unit, and a camming arrangement can be provided coupling the lever to the holder such that pivoting of the lever displaces the holder.

Advantages provided by the present invention include the capability of easily and quickly adjusting the observation and illumination optical axes to obtain optimal convergence and parallax during use by means of a single control which can be arranged in such a way that it can be actuated conveniently both by right-and left-handed users.

The above and other objects, aspects, features and advantages of the present invention will be more readily perceived from the following description of the preferred embodiments thereof taken with the accompanying drawings and appended claims.

BRIEF DESCRIPTION OF THE DRAWINGS

The present invention is illustrated by way of example and not limitation in the figures of the accompanying drawings in which like numbers indicate like parts and in which.

DESCRIPTION OF THE PREFERRED EMBODIMENTS

Figure 1:
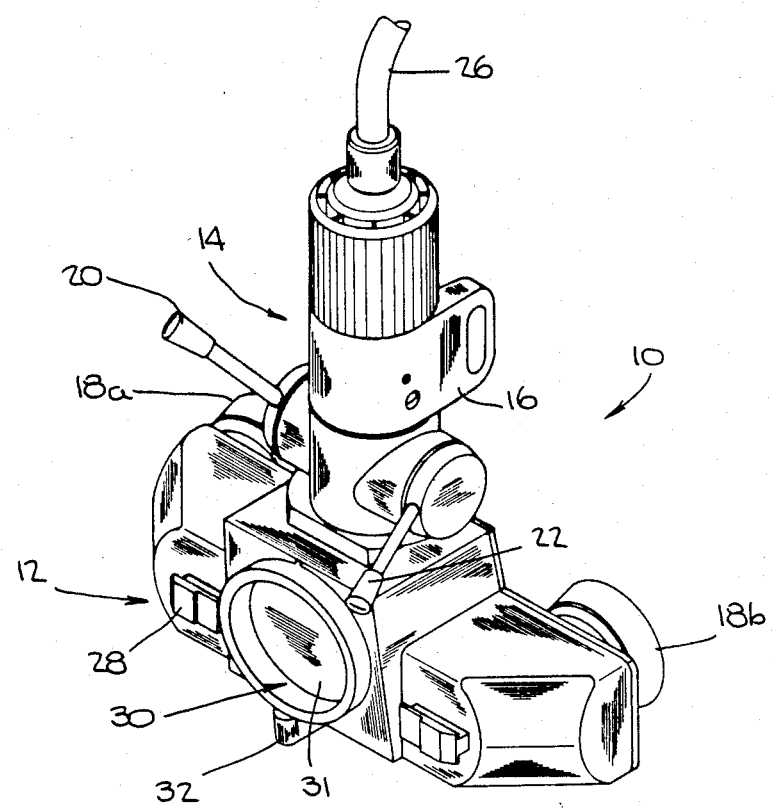
FIG. 1 is a perspective view of a binocular indirect ophthalmoscope according to the present invention.

The binocular ophthalmoscope 10 depicted in FIG. 1 comprises an observation unit 12, and an illumination unit 14 rigidly connected with it. A bracket 16 is secured to the illumination unit 14 and can be used to fasten the ophthalmoscope 10 to a headband (not shown), or to a spectacle frame (not shown). Adjustable eyepieces 18a, 18b are secured to the observation unit 14 through which a user (examiner) observes the pupil of a patient. Levers 20 and 22 can be used to couple luminous-field diaphragms and filters into the path of illumination from the illumination unit 14 to the patient. The illumination unit 14 includes a halogen lamp light source which is supplied with current through the cable 26. Alternatively, fiber optics illumination by means of an external light source and fiber optics cable can be provided. Brackets 28 can be used to attach optical elements for co-observers. The optical aperture or window 30 through whcih light passes between the patient and the observation unit is closed by a plane glass disk 31 to prevent the intrusion of dust into the observation unit. A single lever 32 which is centrally located relative to the observation unit and equally accessible to both left-handed and right-handed users, can be used to simultanelusly set the position of the images of the examiner's pupils and the position of the image of the light source in the patient's pupil, i.e., convergence and parallax.

Figure 2:
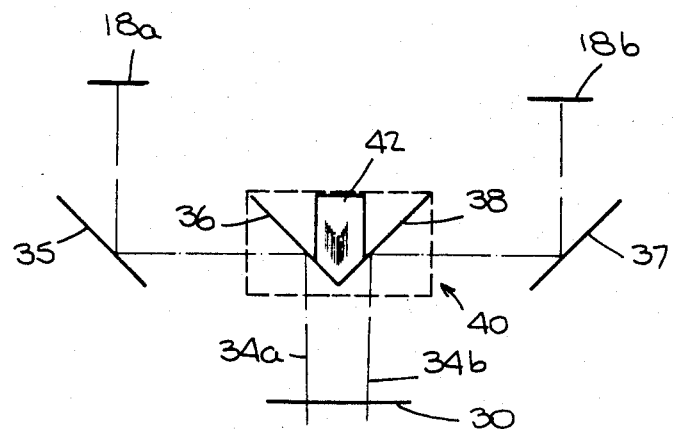
FIG. 2 is a schematic section view of the observation unit of the ophthalmoscope of FIG. 1 illustrating the observation optical axes.

Referring next to FIG. 2, the optical observation axes 34a, 34b or paths in the observation unit 14 between the eyepieces 18a, 18b and the aperture 30 are depicted. Optical observation axis 34a extends from one eyepiece 18a to the aperture 30 and optical observation axis 34b extends from the other eyepiece 18b to the aperture 30. Axis 34a includes a first reflection from mirrow 35 and a second reflection from mirror 36. Axis 34b includes a first reflection from mirror 37 and a second reflection from mirror 38. Mirrors 35 and 37 are stationary, while mirrors 36 and 38 are arranged in a wedge on a holder or carrier 40 which is movable in the plane of observation defined by the observation axis 34a, 34b from the mirrors 36, 38 through the aperture 30. The angular separation of the observation optical paths 34a, 34b in the observation plane can be altered by displacement of the mirror carrier 40.

Figure 3:
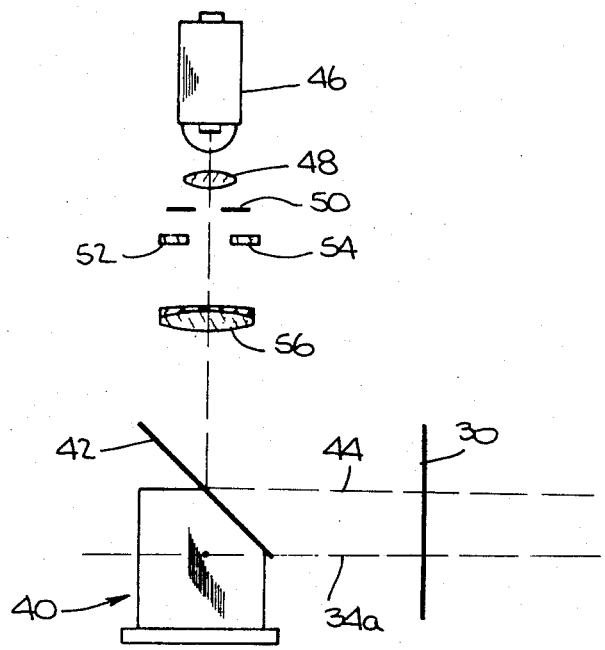
FIG. 3 is a diagrammatic section view of the illumination and observation unit of the ophthalmoscope of FIG. 1 illustrating the illumination optical axis.

Referring next to FIG. 3, the optical axis of illumination from the light source 46 to the aperture 30 is designated 44. Light source 46 projects light through a condensing lens 48 and a diaphragm 50 which is adjustable by the lever 20 depicted in FIG. 1. Optical filters 52, 54 can be placed into and removed from the illumination path by means of the lever 22 depicted in FIG. 1. The objective lens 56 produces an image of the diaphragm 50 at a defined distance in front of the ophthalmoscope. The optical axis of illumination 44 is deflected by the illumination mirror 42 through the aperature 30 in the direction of the patient's eye. The illumination mirror 42 is supported on the mirror carrier 40 together with the two observation mirrors 36 and 38. Displacement of the mirror carrier 40 towards and away from the patient's eye changes the separation of the axis of illumination 44 from the observation plane defined by the optical observation paths 34a, 34b.

Figure 4:
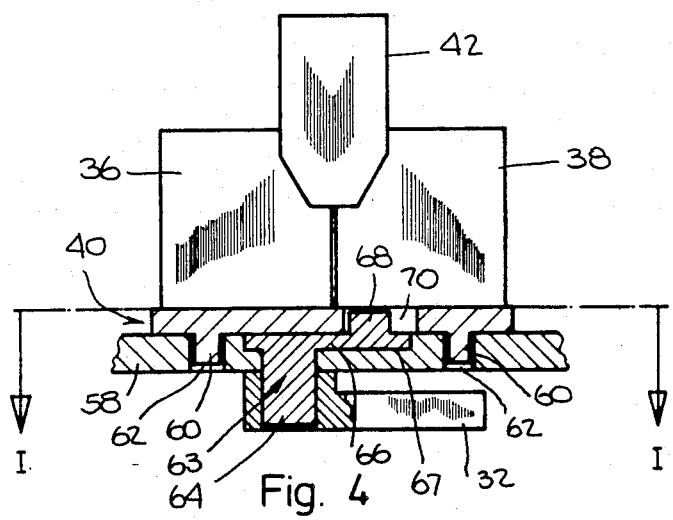
FIG. 4 is a view partially in section of an embodiment of means for moving the observation and illumination mirror of the ophthalmoscope depicted in FIG. 1 by means of a single control to adjust the observation and illumination axes.
Figure 5:
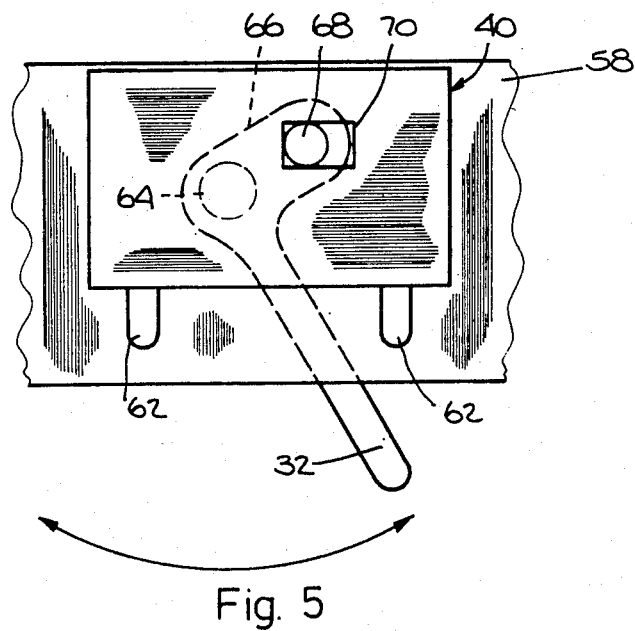
FIG. 5 is a section view of means depicted in FIG. 4, taken along line 5—5 in FIG. 4.

As depicted in FIGS. 4 and 5, the mirror carrier 40 on which are mounted mirrors 36, 38 and 42 slidably rests on a plate 58 forming the interior bottom of the housing of the observation unit 12. The mirror carrier 40 includes two rail-shaped projections 60 which are disposed in and slidably engaged by two slot-shaped recesses 62 in the plate 58, which together form a carriage-like guideway. The recesses 62 extend parallel to the observation plane and parallel to the axis of aperture 30 so that the carrier 40 is displaceable towards and away from the aperture. The lever 32 is pivotally mounted to the plate 58 by means of a pivot 63 rotatably mounted to plate 58. The pivot 63 includes a shaft 64 projecting through an opening in plate 58 outwardly from the bottom of the observation unit, an arm 66 extending at an angle with lever 32 parallel to the bottom of the observation unit in a recess 67 of plate 58, and a cam guide 68 received in a cam recess 70 in the bottom of the mirror carrier 40. The lever 32 is secured to the projecting shaft 64 so that pivoting of the lever rotates the shaft. This causes the cam guide 68 to move the mirror carrier 40 as the cam guide 68 slides in the cam recess 70. In FIG. 5, the lever 32 and arm 66 are depicted schematically as one piece. Pivoting lever 32 along the direction of the arrow displaces the mirror carrier 40 along the slot-shaped recesses 62 towards and away from the aperture 30.

Certain changes and modifications of the embodiments disclosed herein will be readily apparent to those skilled in the art. It is the applicant's intention to cover by the claims all those changes and modifications which could be made to the embodiments of the invention herein chosen for the purpose of disclosure without departing from the spirit and scope of the invention.

What is claimed is:

1. In a binocular stereoscopic viewing device which includes an observation unit, means for projecting light into the observation unit, spaced eyepieces secured to the observation unit through which a user views an object to be observed, an optical aperture into the observation unit through which light passes between the object to be observed and the interior of the observation unit, and optical means disposed in the observation unit for optically coupling the eyepieces and the light-projecting means with the aperture including a first optical element optically coupling one eyepiece and the aperture, a second optical element optically coupling a second eyepiece and the aperture, and a third optical element optically coupling the light projecting means and the aperture, the improvement comprising a support structure which supports the first, second and third optical elements in a predetermined, fixed relationship relative to each other for movement together in said predetermined, fixed relationship within the observation unit and means for moving the support structure including a single user-actuable control.

2. The device according to claim 1 wherein the first, second and third optical elements comprise reflective surfaces, wherein the support structure comprises a holder to which the reflective surfaces are secured in said predetermined, fixed relationship relative to each other, and wherein the moving means comprises means for securing the holder in the observation unit for displacement towards and away from the aperture.

3. The device according to claim 2 wherein the moving means comprises a guideway and a mating guide slidably disposed with respect to each other, one of which is secured to the holder and the other of which is secured to the observation unit.

4. The device according to claim 2 wherein the single user-actuable control is mechanically coupled to the holder and accessible exteriorly of the observation unit such that movement of the control displaces the holder together with the three reflective surfaces.

5. The device according to claim 3 wherein the single user actuable control is a lever pivotally coupled to the observation unit, and the means for moving includes a camming arrangement coupling the lever to the holder such that pivoting of the lever displaces the holder.

6. The device according to claim 5 wherein the camming arrangement comprises a cam guide secured to one of the lever and the holder and a cam recess disposed in the other.

7. The device according to claim 5 wherein the lever is disposed substantially centrally relative to the observation unit so as to be substantially equally accessible to right-handed and left-handed users.

8. A binocular stereoscopic viewing device comprising an observation unit, spaced eyepieces secured to the observation unit through which a user views an object to be observed, and optical aperture into the observation unit through which light passes between the object to be observed and the interior of the observation unit, first, second, and third reflective surfaces and a holder supporting the first, second, and third reflective surfaces in a predetermined, fixed relationship relative to each other for displacement together in said predetermined, fixed relationship within the observation unit, the first, second and third reflective surfaces being optically coupled with the aperture, means for projecting light into the observation unit, means optically coupling a first eyepiece and the first reflective surface, a second eyepiece and the second reflective surface, and the light projecting means and the third reflective surface, guide means associated with the observation unit and the holder for guiding the holder for displacement towards and away from the aperture, a single user-actuable control for moving the holder comprisng a lever pivotally coupled to the observation unit and accessible to the exterior of the observation unit, and means for coupling the lever and the holder such that pivoting of the lever displaces the holder.

9. The device according to claim 8 wherein the aperture has an axis and the guide means comprises at least one recess extending in the observation unit parallel to the aperature axis and at least one guide secured to the holder slidably received in the at least one recess.

10. The device according to claim 8 wherein the aperture has an axis and the guide means comprises a plurality of spaced recesses extending in the observation unit parallel to the aperture axis and a corresponding plurality of spaced guides secured to the holder each of which is slidably received in a respective recess.

11. The device according to claim 9 wherein the means for coupling the lever and the holder is a camming arrangement which comprises a cam recess in the holder and a cam guide secured to the lever which is received in the cam recess.

12. The device according to claim 8 wherein the lever is disposed substantially centrally relative to the observation unit so as to be substantially equally accessible to right-handed and left-handed users.

* * * * *